United States Patent
Binmoeller et al.

(10) Patent No.: US 10,085,763 B2
(45) Date of Patent: *Oct. 2, 2018

(54) APPARATUS AND METHODS FOR MAINTAINING A FORCE UPON TISSUE USING A LOOP MEMBER

(71) Applicant: COOK MEDICAL TECHNOLOGIES LLC, Bloomington, IN (US)

(72) Inventors: Kenneth F. Binmoeller, San Francisco, CA (US); Tyler E. McLawhorn, Winston-Salem, NC (US); Vihar C. Surti, Winston-Salem, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 437 days.

This patent is subject to a terminal disclaimer.

(21) Appl. No.: 14/837,498

(22) Filed: Aug. 27, 2015

(65) Prior Publication Data

US 2015/0366578 A1    Dec. 24, 2015

Related U.S. Application Data

(63) Continuation of application No. 12/913,469, filed on Oct. 27, 2010, now Pat. No. 9,144,428.

(51) Int. Cl.
*A61B 17/10* (2006.01)
*A61B 17/3205* (2006.01)
(Continued)

(52) U.S. Cl.
CPC .... *A61B 17/32056* (2013.01); *A61B 17/0487* (2013.01); *A61B 17/12013* (2013.01);
(Continued)

(58) Field of Classification Search
CPC .......... A61B 17/0487; A61B 17/12013; A61B 17/1285; A61B 17/32056; A61B 2017/0488

See application file for complete search history.

(56) References Cited

U.S. PATENT DOCUMENTS

| 2,856,933 A | 10/1958 | Hildebrand et al. |
| 4,208,827 A | 6/1980 | Starkey |

(Continued)

FOREIGN PATENT DOCUMENTS

| EP | 0891746 | 1/1999 |
| EP | 1859747 | 11/2007 |

(Continued)

OTHER PUBLICATIONS

Extended European search report for EP16164754.0 dated Nov. 18, 2016, 7 pgs.

(Continued)

*Primary Examiner* — Gregory Anderson
(74) *Attorney, Agent, or Firm* — Brinks Gilson & Lione

(57) ABSTRACT

The present embodiments provide apparatus and methods for treating tissue by applying a force to the tissue. In one embodiment, the apparatus comprises a deployable segment having proximal and distal regions, a main body extending therebetween, and a loop member formed at the distal region of the deployable segment. A cannula having a bore is dimensioned to circumferentially surround at least a portion of the main body at a location proximal to the loop member, and a spring member is disposed between the cannula and the loop member. The proximal end of the spring member is affixed to the cannula, and the distal end of the spring member is movable to apply a compressive force to adjust the size of the opening of the loop member and compress tissue disposed within the opening of the loop member. In an alternative embodiment, the cannula is omitted, and a diam- (Continued)

eter of the loop member is configured to be reduced and increased any number of times before final deployment of the deployable segment.

18 Claims, 5 Drawing Sheets

Related U.S. Application Data

(60) Provisional application No. 61/256,430, filed on Oct. 30, 2009.

(51) Int. Cl.
*A61B 17/04* (2006.01)
*A61B 17/12* (2006.01)
*A61B 17/128* (2006.01)
*A61B 17/32* (2006.01)

(52) U.S. Cl.
CPC .. *A61B 17/1285* (2013.01); *A61B 2017/0488* (2013.01); *A61B 2017/12004* (2013.01); *A61B 2017/320064* (2013.01)

(56) References Cited

U.S. PATENT DOCUMENTS

| | | | |
|---|---|---|---|
| 5,054,483 A | 10/1991 | Marten et al. | |
| 5,129,882 A | 7/1992 | Weldon et al. | |
| 5,792,148 A | 8/1998 | Laxvik | |
| 5,855,586 A * | 1/1999 | Habara | A61B 17/12009 606/139 |
| 5,984,917 A | 11/1999 | Fleischman et al. | |
| 6,319,193 B1 | 11/2001 | Arai et al. | |
| 2001/0031970 A1 | 10/2001 | Heuser et al. | |
| 2003/0144673 A1 | 7/2003 | Onuki et al. | |
| 2005/0177022 A1 | 8/2005 | Chu et al. | |
| 2005/0240224 A1 * | 10/2005 | Wu | A61B 17/06166 606/228 |
| 2007/0219571 A1 | 9/2007 | Balbierz et al. | |
| 2008/0051721 A1 | 2/2008 | Carter et al. | |
| 2008/0140095 A1 | 6/2008 | Smith et al. | |
| 2009/0005792 A1 | 1/2009 | Miyamoto et al. | |
| 2009/0222029 A1 | 9/2009 | Gordin et al. | |
| 2010/0160935 A1 | 6/2010 | Karpiel et al. | |

FOREIGN PATENT DOCUMENTS

| | | |
|---|---|---|
| JP | 5-123329 | 5/1993 |
| JP | 11-511362 | 10/1999 |
| JP | 2000-107198 | 4/2000 |
| WO | WO96/28102 | 9/1996 |
| WO | WO97/09935 | 3/1997 |
| WO | WO99/63895 | 6/1999 |
| WO | WO2008/041225 A2 | 4/2008 |

OTHER PUBLICATIONS

Appeal Brief for JP2012-537001 filed Aug. 27, 2015, 8 pgs.
Amendment for JP2012-537001 filed Aug. 27, 2015, 2 pgs.
Notice of Allowance for JP2012-537001 dated Sep. 16, 2015, 4 pgs. including English translation.
International Search Report and Written Opinion for PCT/US2010/054284 dated Jan. 27, 2011, 15 pgs.
Rengen, Mohan, R. et al., "Detachable Snares (Endoloop)", Techniques in Gastrointestinal Endoscopy, Elsevier Inc., 2006, 4 pgs.
PDF of Poster from Digestive Disease Week, May 30-Jun. 4, 2009, Chicago, Illinois, 1 pg.
International Preliminary Report on Patentability for PCT/US2010/054284 dated May 10, 2012, 9 pgs.
Communication Pursuant to Rules 161(1) and 162 EPC for European Patent Application No. 10771882.7 dated Jul. 4, 2012, 2 pgs.
Response to Communication Pursuant to Rules 161(1) and 162 EPC for European Patent Application No. 10771882.7 filed Jan. 10, 2013, 17 pgs.
Examination Report No. 1 for Australian Patent Application No. 2010313426 dated Jun. 25, 2013, 4 pgs.
Office Action for Canadian Patent Application No. 2780122 dated Mar. 28, 2013, 2 pgs.
Response to Office Action for Canadian Patent Application No. 2780122 filed Sep. 23, 2013, 12 pgs.
Notice of Allowance for Canadian Patent Application No. 2780122 dated Dec. 20, 2013, 1 pg.
First Office Action for Chinese Patent Application No. 201080053865.4 dated Apr. 8, 2014, 14 pgs. Including English translation.
Response to Examination Report for Australian Patent Application No. 2010313426 dated May 26, 2014, 8 pgs.
Official Action for European Patent Application 10771882.7 dated Dec. 5, 2014, 4 pgs.
Response to Official Action for European Patent Application 10771882.7 filed Apr. 16, 2015, 11 pgs.
Notice of Acceptance for Australian Patent Application 2010313426 dated May 30, 2014, 2 pgs.
Response to First Office Action for Chinese Patent Application 201080053865.4 filed Aug. 20, 2014, 13 pgs. including English translation
Second Office Action for Chinese Patent Application 201080053865.4 dated Oct. 31, 2014, 10 pgs. including English translation.
Response to Second Office Action for Chinese Patent Application 201080053865.4 filed Jan. 14, 2015, 3 pgs.
Notice of Patent Grant for Chinese Patent Application 201080053865.4 dated Mar. 26, 2015, 4pgs. including English translation.
Office Action for Japanese Patent Application 2012-537001 dated Jul. 15, 2014, 5 pgs.
Response to Office Action for Japanese Patent Application 2012-537001 filed Nov. 14, 2014, 3 pgs (English).
Notice of Allowance for EP10771882.7 dated Oct. 8, 2015, 29 pgs.
Examination Report in European Application No. 16164754.0, dated Nov. 20, 2017, 5 pages.
Office Action in U.S. Appl. No. 14/837,566, dated Nov. 22, 2017, 6 pages.
Examination Report dated May 4, 2018 for European Application No. 16164754.0, 4 pages.

* cited by examiner

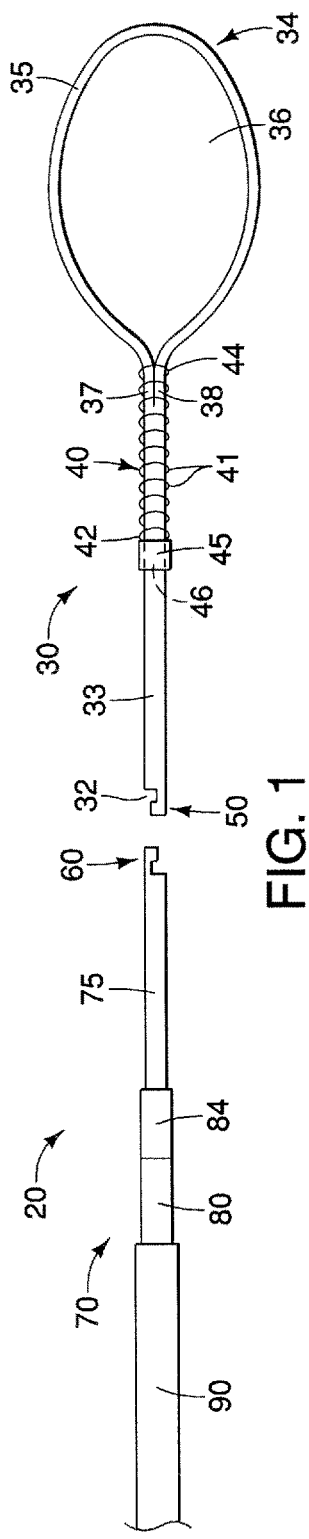
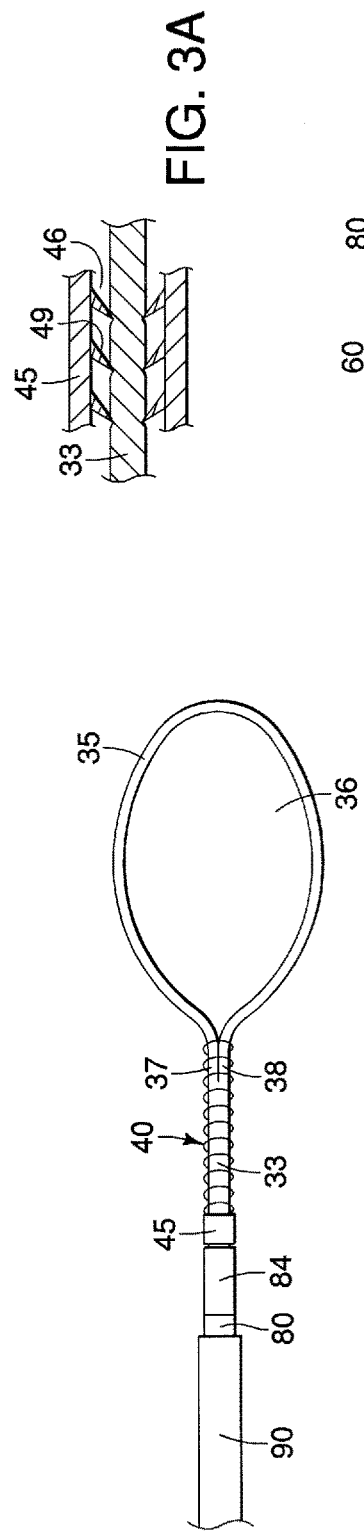
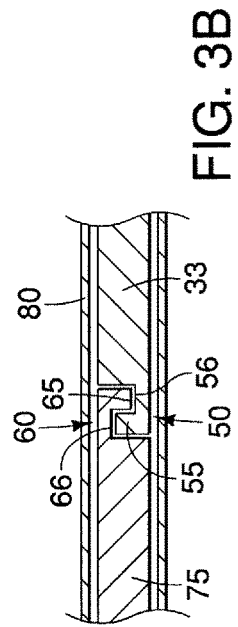

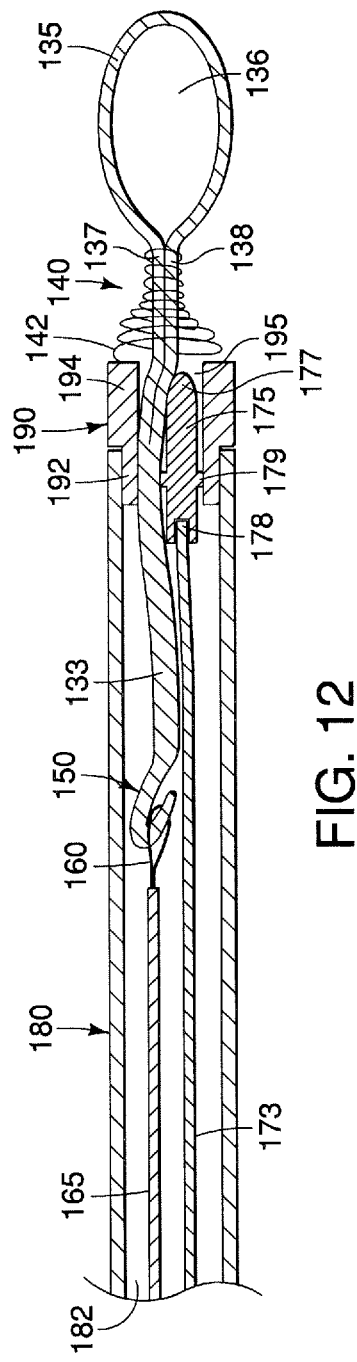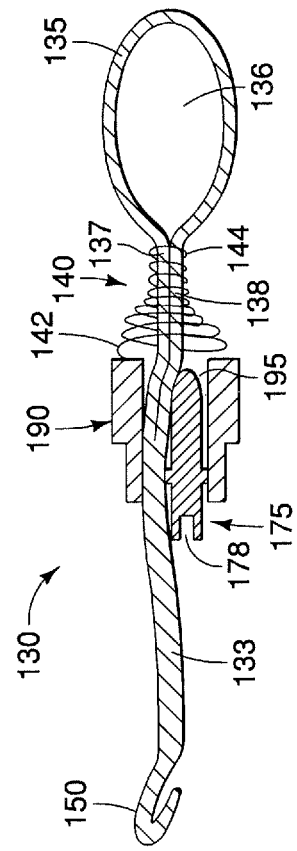

APPARATUS AND METHODS FOR MAINTAINING A FORCE UPON TISSUE USING A LOOP MEMBER

PRIORITY CLAIM

The present patent document is a continuation application that claims the benefit of priority under 35 U.S.C. § 120 of U.S. patent application Ser. No. 12/913,469, filed Oct. 27, 2010, which claims the benefit of the filing date under 35 U.S.C. § 119(e) of Provisional U.S. Patent Application Ser. No. 61/256,430, filed Oct. 30, 2009. All of the foregoing applications are hereby incorporated by reference in their entirety.

BACKGROUND

The present embodiments relate generally to medical devices, and more particularly, to apparatus and methods for maintaining a force upon tissue using a loop member.

There are various instances in which it may become necessary or desirable to deliver a deployable snare into engagement with tissue. For example, such a snare may be used to induce hemostasis during a polypectomy, esophageal variceal bleeding, gastric variceal bleeding, and the excision of gastrointestinal stromal tumors. Further, deployable snares may be useful in ligation of varices or polyps, closure of gastrointestinal fistulas, and other procedures.

There are various commercially available deployable snares. Some of the deployable snares comprise a loop made of nylon, one or more elongated wires, sutures and/or other materials. The size and configuration of the loop may be adjusted using a stopper or cinching member that may be sized to surround first and second ends of the loop. As the stopper or cinching member is distally advanced relative to the loop, the size of the loop may be decreased and a desired amount of force may be imposed upon target tissue.

While such snares are beneficial for providing an initial pressure upon the target tissue, the diameter of the loop generally remains fixed in the original configuration applied by the physician. In particular, the stopper or cinching member maintains the original diameter and configuration of the loop. It has been discovered by the applicants that, as tissue begins to necrose, the shape of the tissue originally enclosed by the loop may change profile, and in particular, may decrease in size. Therefore, if the loop remains in its original fixed configuration, the loop may prematurely fall off of the tissue and fail to maintain a continuous force upon the tissue over an extended period of time.

SUMMARY

The present embodiments provide apparatus and methods for treating tissue by maintaining a force upon the tissue using a loop member. In one embodiment, the apparatus comprises a deployable segment having proximal and distal regions and a main body extending therebetween. A loop member is formed at the distal region of the deployable segment. A cannula having a bore is dimensioned to circumferentially surround at least a portion of the main body at a location proximal to the loop member, and a spring member is disposed between the cannula and the loop member. The proximal end of the spring member is affixed to the cannula, and the distal end of the spring member is movable to apply a compressive force to adjust the size of the opening of the loop member and compress tissue disposed within the opening of the loop member.

Advantageously, the provision of the spring member provides a compressive force to ensure that the loop member closely and continuously surrounds the target tissue. In particular, as the tissue necroses or otherwise changes shape, the spring member causes the loop member to assume a correspondingly reduced diameter. Therefore, unlike other devices having a fixed diameter, the loop member will not prematurely lose its engagement with the target tissue over time.

The apparatus may be delivered using a catheter and stylet arrangement. In one example, a first retainer is disposed at the proximal region of the deployable segment, and a second retainer is disposed at a distal end of the stylet. Longitudinal movement of the stylet effects corresponding longitudinal movement of the deployable segment when the first and second retainers are coupled together. The second retainer is configured to be coupled to the first retainer when a catheter is positioned over both the first and second retainers, and further is configured to be disengaged from the first retainer when no longer covered by the catheter.

In an alternative embodiment, the cannula is omitted, and a diameter of the loop member is configured to be reduced and increased any number of times before final deployment of the deployable segment. Optionally, in either embodiment, a sclerosing agent may be emitted from at least a portion of the loop member to achieve a desired biological effect.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 1 is a side view of a first embodiment of an apparatus for maintaining a force upon tissue with a deployable segment and a delivery segment in an unassembled state.

FIG. 2 is a side view of the apparatus of FIG. 1 in an assembled state.

FIG. 3A is a side sectional view depicting a cannula and a portion of the main body of the deployable segment of FIG. 1.

FIG. 3B is a side sectional view showing the first and second retainers of the apparatus of FIG. 1 in an assembled state.

FIGS. 10-13 are side sectional views of exemplary method steps for using an alternative apparatus to maintain a force upon tissue.

DETAILED DESCRIPTION OF THE PREFERRED EMBODIMENTS

Figure 4:
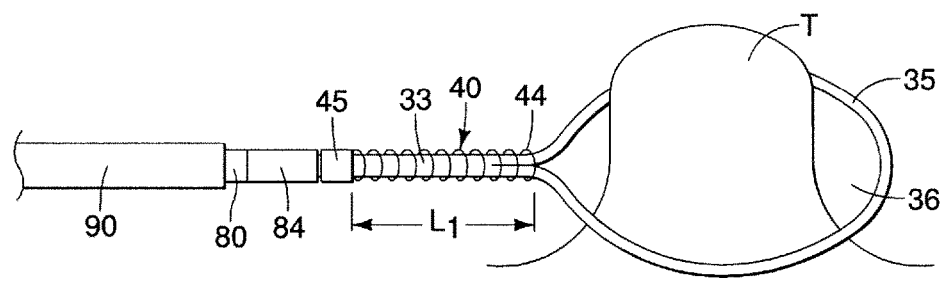
FIGS. 4-7 are schematic views of exemplary method steps for using the apparatus of FIGS. 1-2 to maintain a force upon tissue.

In the present application, the term "proximal" refers to a direction that is generally towards a physician during a medical procedure, while the term "distal" refers to a direction that is generally towards a target site within a patient's anatomy during a medical procedure.

Referring now to FIG. 1, a first embodiment of an apparatus 20 for maintaining a force upon tissue is shown. The apparatus 20 generally comprises a deployable segment 30 and a delivery segment 70. As will be explained in greater detail below, the deployable segment 30 may be disengaged from the delivery segment 70 and remain engaged with tissue to provide a continuous compressive force upon the tissue.

The deployable segment 30 comprises proximal and distal regions 32 and 34, respectively, and a main body 33 extending generally therebetween. The proximal region 32 comprises a first retainer 50, which may be coupled to the delivery segment 70 as explained further below. The distal region 34 comprises a loop member 35 having an opening 36 and first and second ends 37 and 38, as generally shown in FIG. 1. The loop member 35 may be formed from one or more elongated wires or sutures, nylon, nitinol, stainless steel, and/or any combination of the above elements or other elements not specified.

The main body 33 of the deployable segment 30 extends proximally away from the loop member 35. The main body 33 may comprise a portion of the first and second ends 37 and 38 of the loop member when the first and second ends 37 and 38 of the loop member 35 extend adjacent one another in a proximal direction towards the proximal region 32. In this embodiment, a portion of the first and second ends 37 and 38 may be heat shrunk together, or otherwise coupled, a set distance from the loop member 35 to form a substantially cylindrical segment spanning between the proximal and distal regions 32 and 34.

In an alternative embodiment, the main body 33 may comprise a separate member, i.e., distinct from the first and second ends 37 and 38 of the loop member 35. For example, the main body 33 may comprise a length of wire that is coupled to the first and second ends 37 and 38 of the loop member 35 and extends proximally therefrom. The coupling may be achieved using an adhesive, solder, weld, heat shrink tubing, mechanical coupling, or any other suitable means.

Referring still to FIG. 1, the deployable segment 30 further comprises a spring member 40 having a proximal end 42, a distal end 44, and a plurality of turns 41 disposed therebetween. The spring member 40 circumferentially surrounds at least a portion of the main body 33 and the first and second ends 37 and 38 of the loop member 35. Spring member 40 may comprise a compression spring, as shown in the embodiments herein, and may be formed of metal, plastic or another suitable material. Spring member 40 may comprise a variable or constant force spring. Alternatively, spring member 40 may comprise a resilient compressive member that optionally comprises a plurality of turns. In the latter example, the spring member may comprise a solid elastomeric component that may be compressed and impose the compressive forces described herein.

The spring member 40 may comprise a material, shape and configuration that may be tailored based on a given application. In particular, the diameter, wire thickness, stiffness and/or other features of the spring member 40 may be varied as needed for a particular procedure to meet anatomical constraints and/or vary the force imposed on tissue segments. For example, a substantially stiff spring member 40 may provide an increased force upon the loop member 35 to reduce the likelihood of the deployable segment 30 becoming disengaged from tissue after deployment, as explained further in FIGS. 4-7 below.

In the embodiment of FIGS. 1-2, the spring member 40 is disposed between a cannula 45 and the loop member 35. The proximal end 42 of the spring member 40 may be secured to the cannula 45 using an adhesive, solder, weld, mechanical attachment device, or any other suitable mechanism. The main body 33 of the deployable segment 30 extends through a bore 46 of the cannula 45, as best seen in FIGS. 1 and 3A.

In one embodiment, a one-way mechanism is employed wherein the main body 33 of the deployable segment 30 may be advanced in a proximal direction through the cannula 45 with a predetermined pulling force provided by a physician, but the main body 33 cannot be advanced in a distal direction through the cannula 45. As such, the cannula 45 serves as a "stop" for retaining the spring member 40, as explained greater with reference to FIG. 5 below.

An interior region of the bore 46 of the cannula 45 and an exterior portion of the main body 33 may comprise a one-way interlocking mechanism to ensure movement of the main body 33 in a proximal direction only through the cannula 45, or a frictional fit may be employed such that the main body 33 bunches up on a proximal side of the cannula 45 to inhibit distal advancement. For example, in one embodiment depicted in FIG. 3A, teeth 49 may be angled in a proximally direction into the bore 46 of the cannula 45 for causing one-way movement of the main body 33 relative to the cannula 45. The spring member 40 is thus maintained between the cannula 45 and the loop member 35, and likewise can be compressed therebetween to exert a force on the loop member 35. Notably, the cannula 45 may comprise a relatively smaller length collar-like structure, as depicted herein, or may comprise an increased, elongated length.

The delivery segment 70 generally comprises inner and outer catheters 80 and 90, respectively, each having proximal and distal ends and lumens extending therebetween. The inner catheter 80 is configured to be disposed within the lumen of the outer catheter 90, as generally depicted in FIG. 1. A distal region of the inner catheter 80 may be coupled to, or formed integrally with, a reinforcement cannula 84. The reinforcement cannula 84 of the inner catheter 80 may abut the cannula 45 disposed over the main body 33, as depicted in FIG. 2 and explained further below.

The delivery segment 70 further comprises a stylet 75, which has an outer diameter configured for movement within the lumen of the inner catheter 80. In one embodiment, the stylet 75 and the main body 33 comprise generally identical outer diameters, such that both components may be advanced within the lumen of the inner catheter 80 when coupled together.

In order to deliver the deployable segment 30 to a target tissue site using the delivery segment 70, the first retainer 50 of the deployable segment 30 is joined to a second retainer 60 of the delivery segment 70. The second retainer 60 may be formed integral with or coupled to a distal region of the stylet 75.

The stylet 75 extends proximally and may be coupled to a handle that may be manipulated by a physician. In use, the first retainer 50 is joined to the second retainer 60, as explained greater below, and longitudinal movement of the stylet 75 affects sizing of the loop member 35. When a desired sizing of the loop member 35 is achieved, the first retainer 50 is configured to be disengaged from the second retainer 60, leaving only the deployable segment 30 inside the body, as explained in FIGS. 6-7 below.

Various types of complementary first and second retainers 50 and 60 may be used to facilitate controlled release of the deployable segment 30 in accordance with the present embodiments. Suitable complementary first and second retainers 50 and 60 are described in commonly-assigned U.S. patent application Ser. No. 11/807,827, filed May 30, 2007 (hereinafter "the '827 application"), which is hereby incorporated by reference in its entirety. The first and second retainers 50 and 60 shown in the present application therefore are one of multiple possible types of retaining mechanisms for controlled release of the deployable segment 30.

In the embodiment herein, the second retainer 60 is complementary to the first retainer 50 so that the first and second retainers 50 and 60 can be matingly joined. The first retainer 50 has a knob 55 disposed proximal to a notch 56, as shown in FIG. 3B. In a symmetrical manner, the second retainer 60 has a knob 65 disposed distal to a notch 66, as shown in FIG. 3B. The knobs 55 and 65 may approximate the shape of a half-cylinder having a flat surface, as depicted in FIG. 3B, or alternatively may comprises a rounded configuration, as described further in the '827 application.

The first and second retainers 50 and 60 are joined with each other by locating the knob 55 of the first retainer 50 within the notch 66 of the second retainer 60, and by locating the knob 65 of the second retainer 60 within the notch 56 of the first retainer 50. When joined, the first and second retainers 50 and 60 form a substantially continuous cylinder shape having substantially the same outer diameter, as shown in FIG. 3B. The outer diameter of the first and second retainers 50 and 60, when mated, preferably is slightly less than an inner diameter of the inner catheter 80, and further preferably is substantially identical to the outer diameter of the main body 33, as depicted in FIG. 3B.

It should be noted that although the first retainer 50 matingly joins with second retainer 60, they will not retain a joined position unless they are held together. Since the inner catheter 80 comprises an inner diameter that is slightly larger than the mated first and second retainers 50 and 60, the inner catheter 80 therefore holds and maintains the first and second retainers 50 and 60 in a mating position, as long as the inner catheter 80 covers both the mating first and second retainers 50 and 60, as shown in FIG. 3B.

Referring now to FIGS. 4-7, an exemplary use of the apparatus 20 is described. In a first step, the deployable segment 30 may be coupled to the delivery segment 70 outside of the patient's body. The stylet 75 may be loaded into the inner catheter 80 such that the second retainer 60 extends just distal to the reinforcement cannula 84 of the inner catheter 80. The first retainer 50 of the deployable segment 30 is matingly joined with the second retainer 60, as described above. The mating first and second retainers 50 and 60 then are loaded into the inner catheter 80 and advanced in a proximal direction. The deployable segment 30 may be advanced proximally into the inner catheter 80 until the cannula 45 over the main body 33 is adjacent to the reinforcement cannula 84 at the distal end of the inner catheter 80, as depicted in FIG. 4. At this time, the loop member 35 may be provided in a relatively open diameter configuration and disposed distal to the spring member 40. The spring member 40 is in a relaxed state having a length $L_1$, as shown in FIG. 4.

In this state, the outer catheter 90 may be advanced distally over all of the components to enclose the loop member 35. An endoscope may be delivered through patient's anatomy and disposed proximal to target tissue T. The outer catheter 90, with components loaded therein, then may be advanced through a lumen of the endoscope until a distal region of the outer catheter 90 is positioned distal to the endoscope. At this time, the outer catheter 90 may be retracted proximally, relative to the other components, to expose the loop member 35 and distal end of the inner catheter 80, as shown in FIG. 4. The loop member 35 then may be positioned around the target tissue T, under direct endoscopic visualization, and/or using other visualization techniques.

Figure 5:
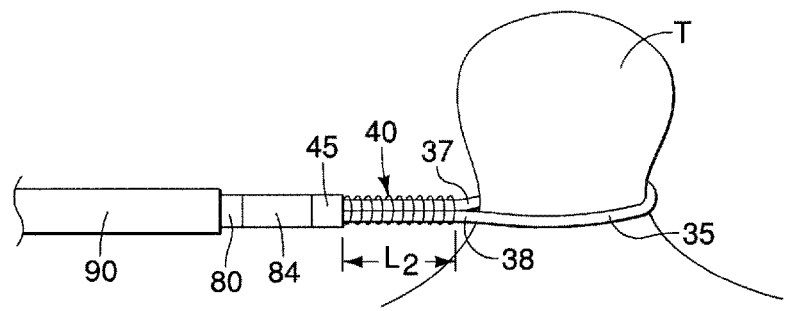

Referring to FIG. 5, in a next step, the size of the loop member 35 may be reduced to apply a compressive force around the target tissue T. In particular, the stylet 75 is retracted in a proximal direction relative to the catheter 80. Since the second retainer 60 of the stylet 75 is engaged with the first retainer 50 of the deployable segment 30 inside of the inner catheter 80, the deployable segment 30 is also retracted in a proximal direction. At this time, the main body 33 of the deployable segment 30 is moved in a proximal direction through the cannula 45, as depicted in FIG. 3A and FIG. 5. As the cannula 45 becomes positioned more distally along the main body 33, the loop member is positioned more proximally relative to the cannula 45 and the spring member 40 compresses.

The inner catheter 80 may be held steady during the retraction of the stylet 75. As the main body 33 and loop member 35 are retracted via the stylet 75, the cannula 45 abuts the reinforcement cannula 84 and cannot be further retracted, thereby limiting the amount of compression of the spring member 40. In effect, the loop member 35 is tightened around the target tissue T while the main body 33 and/or first and seconds ends 37 and 38 are pulled through the stationary cannula 45.

Upon retraction, the loop member 35 compresses the spring member 40 from the relaxed length $L_1$ to a compressed length $L_2$. In particular, the distal end 44 of the spring member 40 is urged proximally by the loop member 35 and/or the tissue T, while the proximal end 42 of the spring member 40 is held stationary by the cannula 40 abutting against the reinforcement cannula 84 of the inner catheter 80.

As noted above, a one-way arrangement may be employed wherein the main body 33 may be advanced only in a proximal direction through the cannula 45, e.g., using a friction fit and/or one-way mechanism. Therefore, when the loop member 35 is tightened around the target tissue T, the main body 33 cannot slide distally relative to the cannula 45 to inadvertently increase the diameter of the loop member 35. At this time, the loop member 35 is tightened around the target tissue T, and the spring member 40 is compressed and pushes in a distal direction against the loop member 35 to promote closure of the loop member 35 around the target tissue T.

Figure 6:
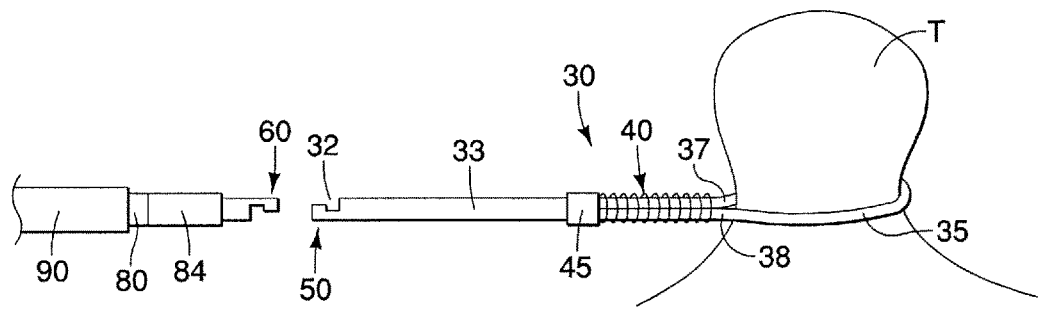

Referring now to FIG. 6, when the loop member 35 is tightened around the target tissue T, the physician may distally advance the stylet 75 relative to inner catheter 80 to expose the junction between the first and second retainers 50 and 60, thereby detaching the retainers and leaving the deployable segment 30 coupled to the target tissue T. Alternatively, the physician may proximally retract the inner catheter 80 relative to the stylet 75 to expose the retainer junction. Once detached, the inner and outer catheters 80 and 90, along with the stylet 75, are removed from the patient.

Figure 7:
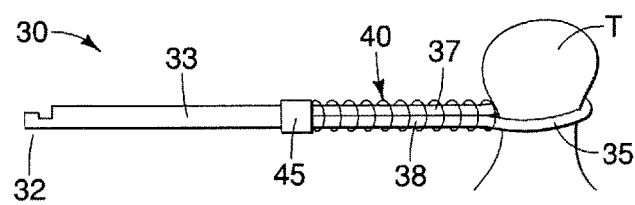

Referring now to FIG. 7, the target tissue T has necrosed over an elapsed period of time. As this happens, the size of the target tissue T has decreased. Advantageously, the provision of the spring member 40 provides a continuous compressive force to ensure that the loop member 35 may be continuously tightened around the target tissue T. In particular, as the tissue necroses, the spring member 40 causes the loop member 35 to assume a correspondingly reduced diameter. Therefore, unlike other devices having a fixed loop diameter, the loop member 35 will not prematurely lose its engagement with the target tissue T as the tissue necroses or otherwise changes shape. Once the target tissue T has been sufficiently treated, then the deployable segment 30 may lose its engagement and pass through the body naturally.

Figure 8:
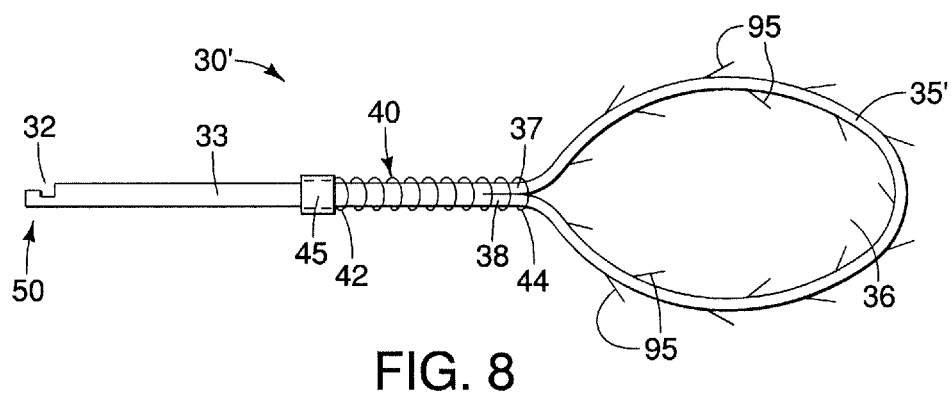
FIG. 8 is a side view of an alternative embodiment of the loop member of FIGS. 1-2.

Referring now to FIG. 8, in an alternative embodiment, a deployable segment 30' is similar to the deployable segment 30 described above, with a main exception that the deployable segment 30' comprises a plurality of barbs 95 that anchor into the tissue T. The provision of the barbs 95 may reduce the likelihood of a loop member 35' slipping off the tissue T while tension is applied to decrease the diameter of the loop member around the tissue. The barbs may be formed integrally with the loop member 35', or attached thereto using soldering or other techniques. Preferably, the barbs are oriented at an angle such that they may be retracted through the spring member 40 with relative ease, as depicted in FIG. 8.

Figure 9:
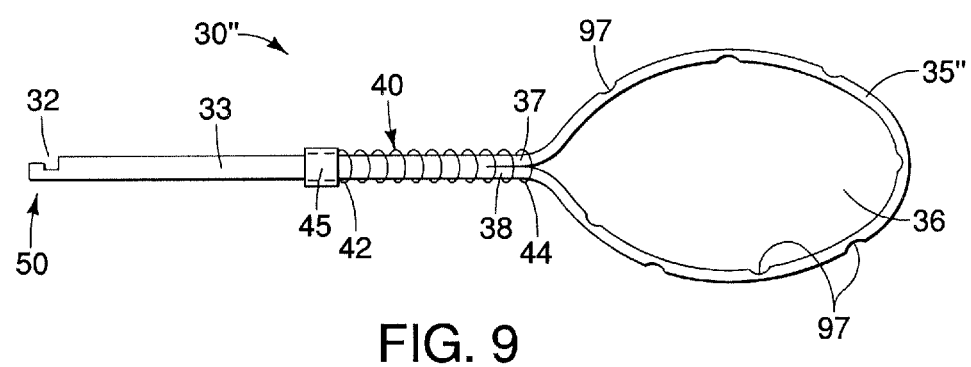
FIG. 9 is a side view of a further alternative embodiment of the loop member of FIGS. 1-2.

Referring now to FIG. 9, in a further alternative embodiment, a deployable segment 30" is similar to the deployable segment 30 described above, with a main exception that the loop member 35" is configured to provide sclerotherapy to promote scar formation, facilitate hemostasis, or perform another desired function. In one example, a sclerosing agent may be delivered through outlet bores 97 formed in an outer surface of a loop member 35". The sclerosing agent may be injected into the bores 97, or the loop member 35" may comprise a lumen therein that houses the sclerosing agent for dispersal through the bores 97. Alternatively, one or more sclerosing agents may be coated onto an outer surface of the loop member 35" for elution into the tissue. While numerous suitable sclerosing agents may be used in conjunction with the loop member 35", one exemplary agent comprises hydroxypolyethoxydodecan.

In a further alternative embodiment, the inner catheter 80 may comprise a torquing member, such as a torque cable, coupled to a portion of the deployable segment 30 to enable rotation of the loop member 35, thereby facilitating orientation and placement of the loop member 35 around target tissue. In this example, the inner catheter 80 may comprise a torque cable to enable rotation of the loop member 35, or another cable may be coupled directly to the deployable segment 30.

Referring now to FIGS. 10-13, in an alternative embodiment, apparatus 120 having loop member 135 is provided for maintaining a force upon tissue. The apparatus 120 generally comprises a deployable segment 130, a stylet 165, a plug member 175, and an outer catheter 180 having a detachable end region 190.

The deployable segment 130 of the apparatus 120 preferably is similar to the deployable segment 30 described above, with a main exception that cannula 45 has been omitted. Moreover, a proximal region 132 of the deployable segment 130 comprises a first retainer 150 in the form of a hook, which may engage and disengage from a second retainer 160 in the form of a loop extending from the stylet 165, as explained greater below. The deployable segment 130 further comprises a main body 133, a distal region 134, and the loop member 135 having an opening 136 therein, as shown in FIG. 10.

Figure 10:
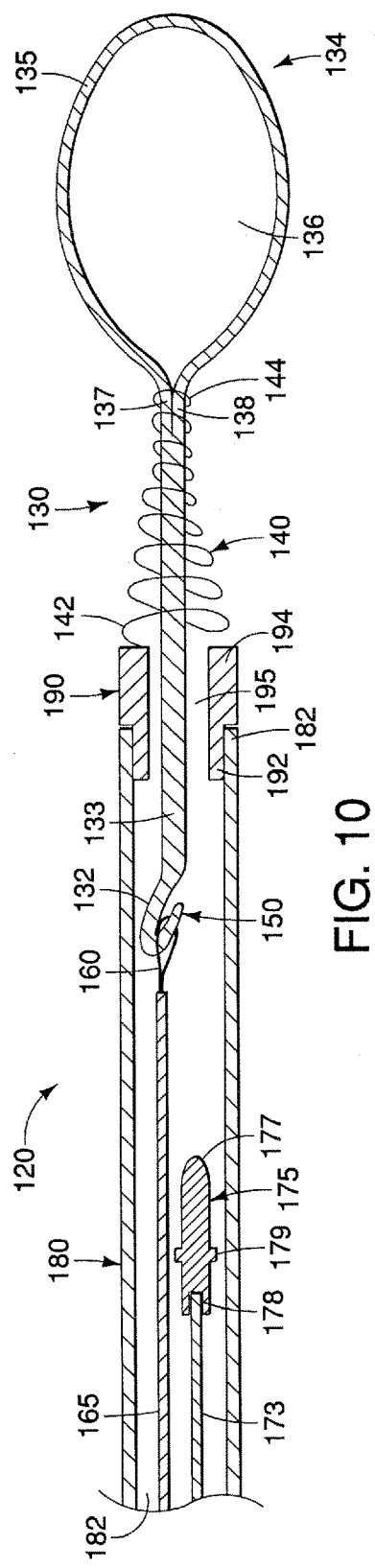

In the embodiment of FIGS. 10-13, the outer catheter 180 comprises a lumen 182 that is sized to receive multiple components. In addition to the stylet 165 coupled to the deployable segment 130, the lumen 182 is sized to receive a stylet 173 that is detachably coupled to the plug member 175. The stylet 173 and the plug member 175 may be disposed adjacent to the stylet 165 within the lumen 182, as depicted in FIG. 10.

The detachable end region 190 comprises proximal and distal segments 192 and 194, respectively, and lumen 195 formed therein. The proximal and distal segments 192 and 194 may form a continuous inner surface, however, the proximal segment 192 has a stepped-down outer diameter compared to the distal segment 194, as shown in FIG. 10. A distal region 182 of the outer catheter 180 may be frictionally coupled around the proximal segment 192 of the detachable end region 190, thereby providing a substantially flush outer diameter as depicted in FIG. 10.

A spring member 140 may be coupled to the distal segment 194 of the detachable end region 190, and extend distally therefrom, as shown in FIG. 10. In this embodiment, the spring member 140 is optionally tapered, such that a larger proximal diameter is attached to the detachable end region 190 and encircles the lumen 195, while a smaller distal diameter is only slightly larger than the main body 133 of the deployable segment 130, as shown in FIG. 10.

In use, the apparatus 120 is delivered towards a target tissue site as generally described above. In particular, a catheter may be used to cover the loop member 135, and the components may be delivery through a lumen of an endoscope. For illustrative purposes, the target tissue is not shown in the embodiments of FIGS. 10-13, but engagement of the loop member 135 with the target tissue would be similar to that shown in FIGS. 4-7 above.

Figure 11:
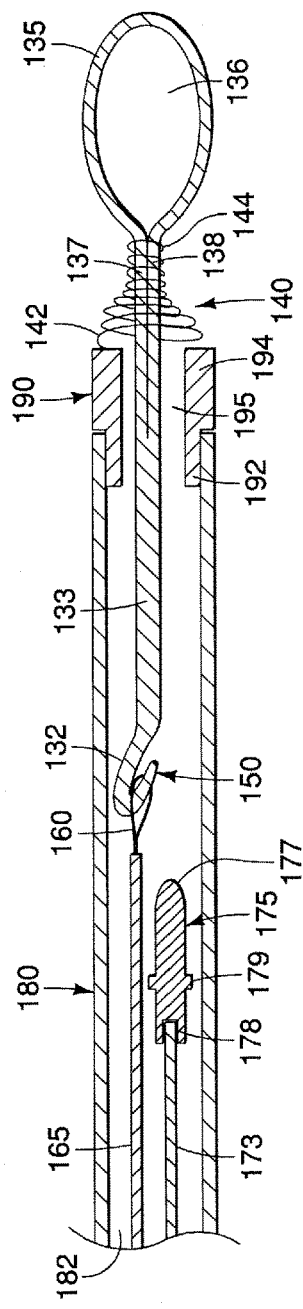

In a first step, the loop member 135 may be positioned around the target tissue, under direct endoscopic visualization and/or using other visualization techniques, as generally described above. In a next step, depicted in FIG. 11, the size of the loop member 135 may be reduced to apply a compressive force around the target tissue. In particular, the stylet 165 is retracted in a proximal direction. Since the second retainer 160 of the stylet 165 is engaged with the first retainer 150 of the deployable segment 130, the deployable segment 130 is also retracted in a proximal direction. At this time, the main body 133 of the deployable segment is moved in a proximal direction through the spring member 140, as depicted in FIG. 11.

Preferably, the outer catheter 180 is held steady during the retraction of the stylet 165 and the loop member 130. Accordingly, the loop member 135 is tightened around the target tissue, and the main body 133 and/or first and seconds ends 137 and 138 are pulled through the spring member 140. Upon retraction, the loop member 135 compresses the spring member 140 from the relaxed length shown in FIG. 10 to the compressed length shown in FIG. 11.

Advantageously, in this embodiment, a physician may increase and reduce the initial diameter of the loop member 135 around the tissue as many times as desired. For example, after the stylet 165 has been retracted to reduce the diameter of the loop member 135 as shown in FIG. 11, if the sizing is not desirable then the physician may simply distally advance the stylet 165 to cause distal advancement of the loop member 135 to increase the size of the loop member 135. This sequence of advancement and retraction of the stylet 165, and corresponding changes to the size of the loop member 135, may be performed as needed during initial sizing of the loop member 135 around the tissue.

Referring to FIG. 12, when a desired sizing of the loop member 135 around the tissue has been achieved, the stylet 173 coupled to the detachable plug member 175 is distally advanced within the lumen 182 of the outer catheter 180. The stylet 173 is advanced until a distal region 177 of the detachable plug member 175 is wedged adjacent to the main body 133 of the deployable segment 130 within the lumen 195 of the detachable end region 190, as shown in FIG. 12. In this embodiment, the detachable plug member 175 may comprise an elastomeric or other suitable material having a proximal bore 178 that is sized to engage a distal end of the stylet 173 using a friction fit. The distal region 177 may comprise a tapered end to facilitate distal advancement within the lumen 182 of the outer catheter 180, and subsequently into the lumen 195 of the detachable end region 190, as depicted in FIG. 12. Moreover, radial protrusions 179 may be provided on the detachable plug member 175 to promote a secure engagement between the main body 133, the detachable plug member 175, and the detachable end region 190. In the state shown in FIG. 12, the positioning of the main body 133 and loop member 135 are fixed relative to the compressed spring member 140.

In a next step, a physician may proximally retract the outer catheter 180 relative to the stylet 165 to expose the junction between the first and second retainers 150 and 160, thereby detaching the retainers. Further, proximal retraction of the outer catheter 180 relative to the detachable end region 190, beyond a predetermined frictional force threshold, will cause detachment of the detachable end region 190 from the outer catheter 180. Similarly, proximal retraction of the stylet 173, beyond a predetermined frictional force threshold, will cause detachment of the plug member 175 from the stylet 173. Once detached, the outer catheter 180, along with the stylets 165 and 173, are removed from the patient, leaving the deployable segment 130 coupled to the target tissue, as shown in FIG. 13. The plug member 175 and detachable end region 190 remain engaged with the deployable segment 130.

As noted above, the target tissue within the loop member 135 will necrose over an elapsed period of time. As this happens, the size of the target tissue may decrease. Advantageously, the provision of the spring member 140 provides a continuous compressive force to ensure that the loop member may continuously surround the target tissue. In particular, as the tissue necroses, the spring member 140 causes the loop member 135 to assume a correspondingly reduced diameter, such that the loop member 135 will not prematurely lose its engagement with the target tissue as the tissue necroses or otherwise changes its shape. Once the target tissue has been sufficiently treated, e.g., reduced to a significantly reduced size, then the deployable segment 130, the plug member 175 and the detachable end region 190 may pass through the body naturally.

In further alternative embodiments, the spring members 40 and 140 described above may be omitted, and the loop members 35 and 135 may comprise materials that are sensitive to pH, temperature and/or light. In such embodiments, the user may place the loop member around the target tissue with a desired initial amount of tension, as described above. When the loop member is introduced to the pH or temperature of the gastric system or other bodily conduit, or exposed to light from an endoscope, the diameter of the loop member, may decrease to maintain further compression upon the target tissue. Suitable pH sensitive materials comprise chitosan and polyacrylic acid, while a suitable temperature sensitive material comprises polyolefin, and a suitable light sensitive material comprises Azobenzene-based photodevices. In still further alternative embodiments, the loop member may comprise a biodegradeable material that is configured to degrade after a suitable force has been applied to the target tissue over a desired period of time.

In an alternative method, the apparatuses 20 and 120 described above may be used for substantially full-thickness excision of tissue, including gastrointestinal stromal tumors (GIST). In this method, a tissue retractor may be used to pull the entire GIST into the loop member 35 or 135. The loop member 35 or 135 then may be deployed, as explained above, to strangulate blood supply to the GIST, resulting in necrosis and sloughing. Scar formation at the looping site prevents perforation of the tissue wall. Such a method is an improvement that may yield fewer complications relative to current techniques involving excision of the tissue and subsequent attempts to close the perforation in a second step.

In yet a further alternative method, the loop member 35 described herein may be used to close defects, such as perforations, within the gastrointestinal tract. In this example, the loop member 35 may be used in conjunction with a tissue retraction member to bunch tissue surrounding the defect together before deployment of the loop member 35. For example, the tissue retraction member may comprise a balloon or tacking device that is disposed through the opening and used to form a polyp-like section of tissue surrounding the opening, as generally described in U.S. Patent Application Ser. No. 61/256,619 ("the '619 application"), filed Oct. 30, 2009, which is hereby incorporated by reference in its entirety. The tissue retraction member may be advanced in a distal direction through the bodily opening with the tissue retraction member in a contracted state, then is actuated from the contracted state to an expanded state at a location distal to the opening, as explained in the '619 application. Then, the tissue retraction member may be proximally retracted to engage first and second serosal tissue regions at least partially surrounding the opening, thereby causing the first and second serosal regions to be disposed in an adjacent relationship in a polyp-like manner. At this time, the loop member 35 of the present embodiments may be placed around the first and second serosal tissue regions and deployed to apply and maintain a compressive force, as generally explained above, thereby holding the tissue regions together to close the opening.

As an alternative to using a balloon or tacking device as the tissue retraction member, a T-shaped anchor may be placed through the defect. In this embodiment, after the T-shaped anchor is placed through the defect, sutures coupled to the T-shaped anchor may be retracted to cause the first and second serosal regions to be disposed in an adjacent relationship in a polyp-like manner. Subsequently, the loop member 35 may be advanced over the sutures and tightened around the adjacent tissue segments to hold them together. Alternatively, two or more different T-shaped anchors may be placed through tissue surrounding the defect, then retracted proximally to create a polyp-like bundle that the loop member 35 may be placed over.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. Apparatus for treating tissue by applying a force to the tissue, the apparatus comprising:
a deployable segment having proximal and distal regions, and a main body extending therebetween;
a loop member formed at the distal region of the deployable segment, the loop member defining an opening that is adjustable in size;
a cannula having a bore extending therethrough, wherein the cannula is dimensioned to circumferentially surround at least a portion of the main body at a location proximal to the loop member;
an advanceable segment disposed between the cannula and the loop member, the advanceable segment having proximal and distal ends, and dimensioned to circumferentially surround at least a portion of the main body, wherein the proximal end of the advanceable segment is coupled to the cannula, and wherein the distal end of the advanceable segment is movable to apply a compressive force to adjust the size of the opening of the loop member and compress tissue disposed within the opening of the loop member,
wherein the distal end of the advanceable segment moves distally to cause the loop member to close; and
a delivery segment that can be disengaged from the deployable segment, wherein the loop is adjustable while the deployable segment is disengaged from the delivery segment.

2. The apparatus of claim 1 wherein the proximal end of the advanceable segment is secured to the cannula in a fixed relationship.

3. The apparatus of claim 1 wherein the advanceable segment comprises a spring member.

4. The apparatus of claim 3 wherein the loop member causes compression of the spring member when the main body is retracted in a proximal direction through the cannula.

5. The apparatus of claim 1 wherein the cannula frictionally engages the main body of the loop member.

6. The apparatus of claim 5 wherein the advanceable segment comprises a spring member that does not have sufficient force to overcome the friction between the cannula and the main body.

7. The apparatus of claim 5 wherein the main body of the deployable segment is configured for longitudinal movement only in a proximal direction through the cannula.

8. The apparatus of claim 7 further comprising teeth angled in a proximal direction into the bore of the cannula for causing one-way movement of the main body relative to the cannula.

9. The apparatus of claim 1 further comprising at least one barb coupled to the loop member and dimensioned for engaging the tissue.

10. Apparatus for treating tissue by applying a force to the tissue, the apparatus comprising:
a deployable segment having proximal and distal regions, and a main body extending therebetween;
a loop member formed at the distal region of the deployable segment, the loop member defining an opening that is adjustable in size;
a cannula having a bore extending therethrough, wherein the cannula is dimensioned to circumferentially surround at least a portion of the main body at a location proximal to the loop member;
an advanceable segment disposed between the cannula and the loop member, the advanceable segment having proximal and distal ends, and dimensioned to circumferentially surround at least a portion of the main body, wherein the proximal end of the advanceable segment is disposed adjacent to the cannula, and wherein the distal end of the advanceable segment is movable to apply a compressive force to adjust the size of the opening of the loop member and compress tissue disposed within the opening of the loop member,
wherein the distal end of the advanceable segment moves distally to cause the loop member to close; and
a delivery segment that can be disengaged from the deployable segment, wherein the loop is adjustable while the deployable segment is disengaged from the delivery segment.

11. The apparatus of claim 10 wherein the proximal end of the advanceable segment is secured to the cannula in a fixed relationship.

12. The apparatus of claim 10 wherein the advanceable segment comprises a spring member.

13. The apparatus of claim 12 wherein the loop member causes compression of the spring member when the main body is retracted in a proximal direction through the cannula.

14. The apparatus of claim 10 wherein the cannula frictionally engages the main body of the loop member.

15. The apparatus of claim 14 wherein the advanceable segment comprises a spring member that does not have sufficient force to overcome the friction between the cannula and the main body.

16. The apparatus of claim 14 wherein the main body of the deployable segment is configured for longitudinal movement only in a proximal direction through the cannula.

17. The apparatus of claim 16 further comprising teeth angled in a proximal direction into the bore of the cannula for causing one-way movement of the main body relative to the cannula.

18. The apparatus of claim 10 further comprising at least one barb coupled to the loop member and dimensioned for engaging the tissue.

* * * * *